United States Patent
Li et al.

(10) Patent No.: US 9,234,830 B2
(45) Date of Patent: Jan. 12, 2016

(54) WAREHOUSE SYSTEM AND METHOD FOR DETECTING AIR PARTICLES

(71) Applicant: Shenzhen China Star Optoelectronics Technology Co., Ltd., Shenzhen, Guangdong (CN)

(72) Inventors: Chenyangzi Li, Shenzhen (CN); Chunhao Wu, Shenzhen (CN); Kunhsien Lin, Shenzhen (CN); Minghu Qi, Shenzhen (CN); Yongqiang Wang, Shenzhen (CN); Zenghong Chen, Shenzhen (CN); Yunshao Jiang, Shenzhen (CN); Zhenhua Guo, Shenzhen (CN); Zhiyou Shu, Shenzhen (CN); Guokun Yang, Shenzhen (CN)

(73) Assignee: Shenzhen China Star Optoelectronics Technology Co., Ltd, Shenzhen, Guangdong (CN)

(*) Notice: Subject to any disclaimer, the term of this patent is extended or adjusted under 35 U.S.C. 154(b) by 415 days.

(21) Appl. No.: 13/808,581

(22) PCT Filed: Dec. 17, 2012

(86) PCT No.: PCT/CN2012/086762
§ 371 (c)(1),
(2) Date: Jan. 5, 2013

(87) PCT Pub. No.: WO2014/089854
PCT Pub. Date: Jun. 19, 2014

(65) Prior Publication Data
US 2014/0182359 A1 Jul. 3, 2014

(30) Foreign Application Priority Data
Dec. 12, 2012 (CN) .......................... 2012 1 0535620

(51) Int. Cl.
*G01N 15/08* (2006.01)

(52) U.S. Cl.
CPC .......... *G01N 15/082* (2013.01); *B01D 2273/18* (2013.01); *G01N 2015/084* (2013.01)

(58) Field of Classification Search
CPC ............. B01D 2273/18; G01N 15/082; G01N 2015/084
USPC ..................................................... 73/40, 40.7
See application file for complete search history.

(56) References Cited

U.S. PATENT DOCUMENTS 4,324,568 A * 4/1982 Wilcox et al. .................. 95/286
4,494,403 A * 1/1985 Bowers et al. ................. 73/40.7
(Continued)

FOREIGN PATENT DOCUMENTS

JP          05029184 A *    2/1993    .............. H01L 21/02

OTHER PUBLICATIONS

English Machine Translation of Sano et al, JP 05029184 A, Feb. 1993, Translated Apr. 2015.*

(Continued)

*Primary Examiner* — Hezron E Williams
*Assistant Examiner* — David Z Huang
(74) *Attorney, Agent, or Firm* — Andrew C. Cheng (57) ABSTRACT

A warehouse system and method for detecting air particles in a warehouse are disclosed. The warehouse system includes storage locations, air filters, a cartridge, and a control base. The air filters are correspondingly arranged on outer sides of each storage location. A detecting module of the cartridge detects the air particles on a surface of corresponding air filter of the abnormal storage locations. The detecting module further calculates a radius of the air particles and transmits the radius of the air particles to the control base. The control base determines if the corresponding air filter of the abnormal storage locations has leaked. The detecting process of the claimed invention is safer, more precise and convenient.

12 Claims, 7 Drawing Sheets

(56) References Cited

U.S. PATENT DOCUMENTS

| | | | |
|---|---|---|---|
| 5,856,623 A * | 1/1999 | Ahn et al. | 73/863.03 |
| 7,520,668 B2 * | 4/2009 | Chen | 374/121 |
| 2006/0187070 A1 * | 8/2006 | Liang et al. | 340/607 |
| 2006/0266133 A1 * | 11/2006 | Kim et al. | 73/865.5 |
| 2007/0163216 A1 * | 7/2007 | Smasal et al. | 55/446 |
| 2008/0118027 A1 * | 5/2008 | Gaved et al. | 378/37 |
| 2011/0107819 A1 * | 5/2011 | Chung et al. | 73/40.7 |

OTHER PUBLICATIONS

English Machine Translation of Kim et al (KR 10 2001 0015644), Oct. 5, 2002, Translated Jul. 2015.*

* cited by examiner

WAREHOUSE SYSTEM AND METHOD FOR DETECTING AIR PARTICLES

BACKGROUND OF THE INVENTION

1. Field of the Invention

Embodiments of the present disclosure relate to warehouse technology, and more particularly to a warehouse system and method for detecting air particles.

2. Discussion of the Related Art

As automatic warehouse systems require a dust free environment, usually, air filters are installed in the warehouse so as to absorb air particles, such as acidic or basic air particles, or liquid particles.

Typically, the detecting process to determine if the air filters have leaked is conducted by human labors. Specifically, operators stand on mechanical arms of lifting apparatuses and use the detector to detect air particles on a surface of the air filters when the operators are lifted at a predetermined altitude.

However, the above detecting process has problems. First, the detecting process is not convenient and safe. As the operators have to stand on the mechanical arms, accidents may happy due to incorrect operations of the lifting apparatus or incautious operators. Second, the detecting results may not be precise enough for the reason that the detecting process is performed by human labors.

SUMMARY

The object of the claimed invention is to provide a warehouse system and method for detecting air particles in warehouses. The warehouse system and method are capable of determining if the air filters have leaked.

In one aspect, a method for detecting air particles in a warehouse includes: arranging a detecting module in a cartridge; a first detecting step for detecting an amount of air particles of abnormal storage locations of the warehouse; transporting the cartridge to the abnormal storage locations by a transmitting assembly; a second detecting step for detecting the an particles on a surface of corresponding an filters of the abnormal storage locations: calculating a radius of the air particles and transmits the radius to a control base by a communication module; determining if the corresponding air filter of the abnormal storage locations has leaked according to the radius of the air particles; wherein the detecting module includes a detecting probe, and the second detecting step further includes: driving the detecting probe to move; absorbing the air particles on the surface of the corresponding air filter of the abnormal storage locations when the detecting probe is driven to move; the determining step further includes: saving the radius of the air particles detected by the detecting module, and calculating the accumulative air particles within a predetermined particle radius so as to determine if the amount of the accumulative air particles is larger than a threshold; and determining that the corresponding air filter of the abnormal storage locations has leaked if the amount of the accumulative air particles is larger than the threshold.

Wherein a dimension of the moving area of the detecting probe equals to the dimension of the air filter.

In another aspect, a method for detecting air particles in a warehouse includes: arranging a detecting module in a cartridge; a first detecting step for detecting an amount of air particles of abnormal storage locations of the warehouse; transporting the cartridge to the abnormal storage locations by a transmitting assembly; a second detecting step for detecting the air particles on a surface of corresponding air filters of the abnormal storage locations; calculating a radius of the air particles and transmits the radius to a control base by a communication module; and determining if the corresponding air filter of the abnormal storage locations has leaked according to the radius of the air particles.

Wherein the detecting module includes a detecting probe, and the second detecting step further includes: driving the detecting probe to move; and absorbing the air particles on the surface of the corresponding air filter of the abnormal storage locations when the detecting probe is driven to move.

Wherein the determining step further includes: saving the radius of the air particles detected by the detecting module, and calculating the accumulative air particles within a predetermined particle radius so as to determine if the amount of the accumulative air particles is larger than a threshold; and determining that the corresponding air filter of the abnormal storage locations has leaked if the amount of the accumulative air particles is larger than the threshold.

Wherein a dimension of the moving area of the detecting probe equals to the dimension of the air filer.

In another aspect, a warehouse system for detecting air particles includes: a warehouse includes a plurality of storage locations, wherein the storage locations includes abnormal storage locations with an excessive amount of air particles; air filters correspondingly arranged on outer sides of each storage location for filtering the air particles in the storage locations a cartridge comprising a detecting module; a transmitting assembly for transporting the cartridge to the abnormal storage locations such that the detecting module detects the air particles on a surface of the air filters of the corresponding abnormal storage locations; wherein the detecting module further calculates a radius of the air particles and transmits the radius of the air particles to the control base; and the control base determines if the corresponding air filter of the abnormal storage locations has leaked.

Wherein the detecting module further includes a driving assembly, a detecting probe, a particle detector, and a communication module, wherein: the driving assembly drives the detecting probe to move; the detecting probe is for absorbing the air particles on the surface of the corresponding air filter of the abnormal storage locations when the detecting probe is driven to move; the particle detector connects with the detecting probe to calculate the radius of the air particles detected by the detecting probe, and to transmit the radius to the communication module; and the communication module transmits the radius to the control base via wireless communications.

Wherein the control base saves the radius of the air particles detected by the detecting module, and calculates the accumulative air particles within the predetermined particle radius to determine if the amount of the accumulative air particles is larger than the threshold; and the control base determines that the corresponding air filter of the abnormal storage locations has leaked if the amount of the accumulative air particles is larger than the threshold.

Wherein the detecting probe is arranged on a top portion of the cartridge before the detecting process begins, and a top of the detecting probe rotates through 90 degrees and rises up above the surface of the cartridge alter the detecting process begins.

Wherein a distance between the top of the detecting probe and a top portion of the air filter is of a range between 50 mm to 100 mm.

Wherein the driving assembly includes a first driving component and a second driving component, the first driving component drives the detecting probe along a first direction, the second driving component drives the detecting probe along a second direction, and the first direction is orthogonal to the second direction.

Wherein a dimension of the moving area of the detecting probe equals to the dimension of the air filter.

Wherein the driving assembly is installed on a top portion of the cartridge.

Wherein the driving assembly is installed on a side portion of the cartridge.

DETAILED DESCRIPTION OF THE EMBODIMENTS

Embodiments of the invention will now be described more fully hereinafter with reference to the accompanying drawings, in which embodiments of the invention are shown.

Figure 1:
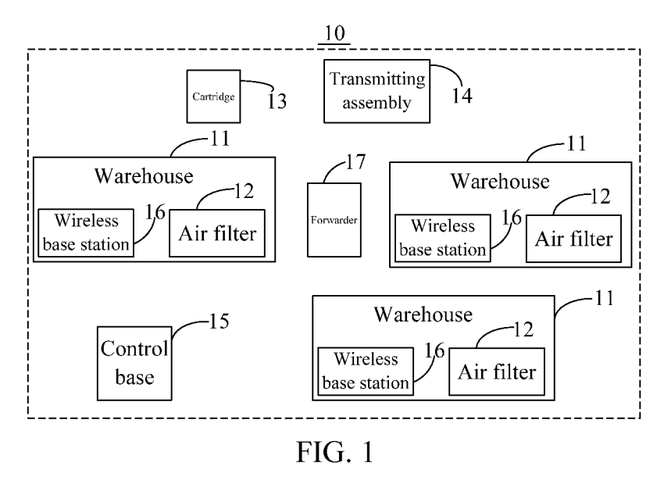
FIG. 1 is a schematic view of the warehouse system for detecting air particles in accordance with a first embodiment.
Figure 2:
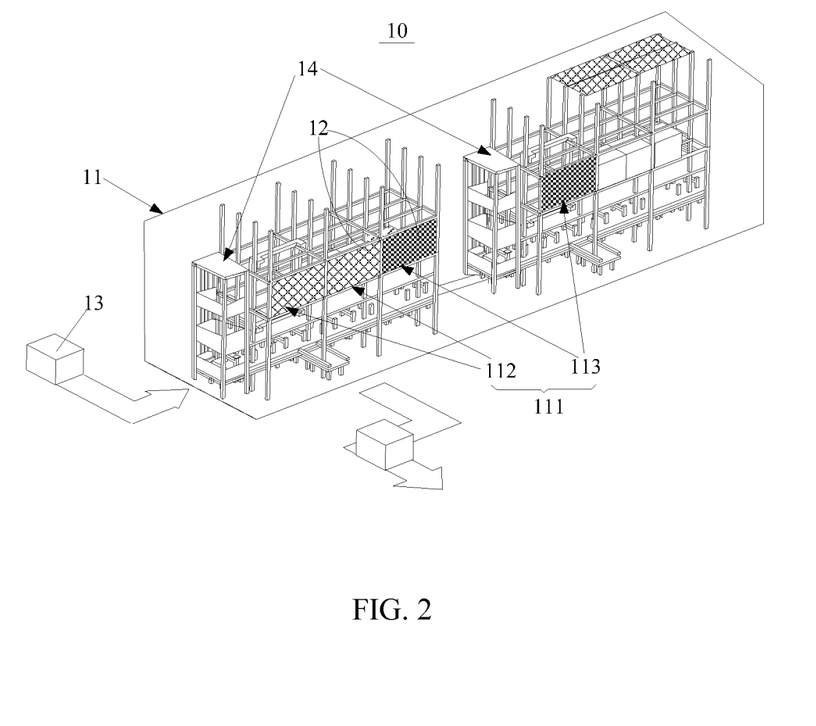
FIG. 2 is a partial perspective view of the warehouse system of FIG. 1.

FIG. 1 is a schematic view of the warehouse system for detecting air particles ("the system") in accordance with a first embodiment. FIG. 2 is a partial perspective view of the warehouse system of FIG. 1. Referring to FIGS. 1 and 2, the system 10 includes a warehouse 11, air filters 12, a cartridge 13, a transmitting assembly 14, a control base 15, a wireless base station 16, and a forwarder 17.

In the embodiment, each warehouse 11 includes a plurality of storage locations 111. The storage locations 111 may be normal storage locations 112 or abnormal storage locations 113. The abnormal storage locations 113 relate to storage locations with an excessive amount of air particles. The process to determine the abnormal storage location will be described hereinafter.

The particle detector of the PMS (power production management) system extracts gas equaling to one cubic foot to calculate the accumulative air particles within a predetermined particle radius. One storage location is determined as abnormal when the amount of the accumulative air particles is larger than a threshold. Table 1 shows several reference ranges for determining if one storage location is normal or not.

TABLE 1

| U209E | 0-0.3µ | 0.3-0.5µ | 0.5-1µ | 1-3µ | 3-5µ | 5-1µ | Sum |
|---|---|---|---|---|---|---|---|
| Accumulative amount for 10-Class | 30 | 10 | 0 | 0 | 0 | 0 | 30 |
| Accumulative amount for 100-Class | 297 | 97 | 20 | 1 | 0 | 0 | 297 |

TABLE 1-continued

| U209E | 0-0.3µ | 0.3-0.5µ | 0.5-1µ | 1-3µ | 3-5µ | 5-1µ | Sum |
|---|---|---|---|---|---|---|---|
| Accumulative amount for 1000-Class | 3000 | 1000 | 226 | 20 | 7 | 0 | 3000 |

It is to be noted that the reference ranges in Table 1 may be adjusted in accordance with real scenarios.

The air filters 12 are correspondingly arranged on outer sides of each storage location 111. In order to clearly illustrate the structure of the system 10, only some of the air filters 12 are shown.

Figure 3:
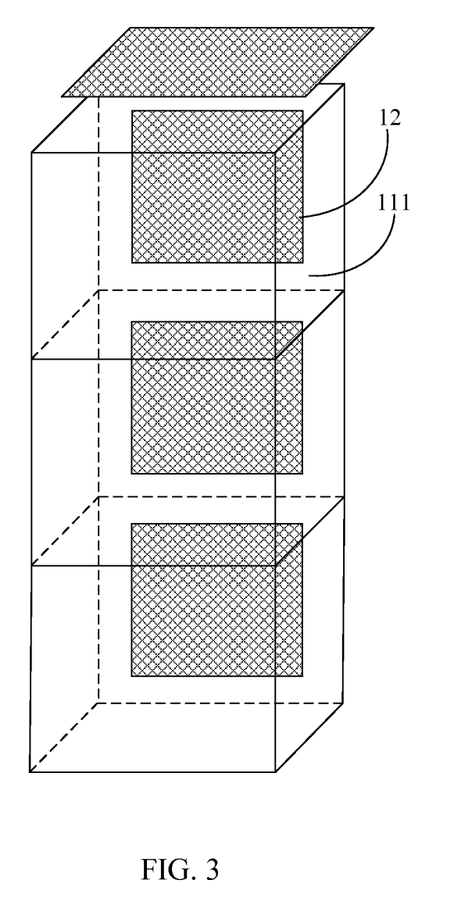
FIG. 3 is a schematic view showing the location of the air filter of FIG. 1.

Referring to FIG. 3, the air filters 12 are arranged on inner side of each storage locations 111, or are arranged on a top surface of the top storage location 111.

Figure 4:
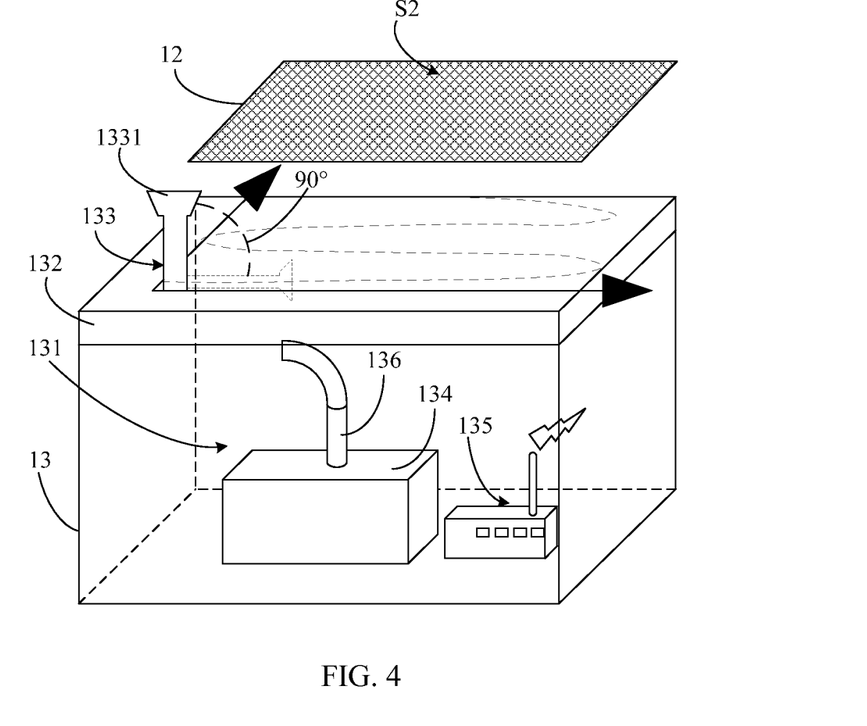
FIG. 4 is a perspective view of the cartridge of the warehouse system of FIG. 1.
Figure 5:
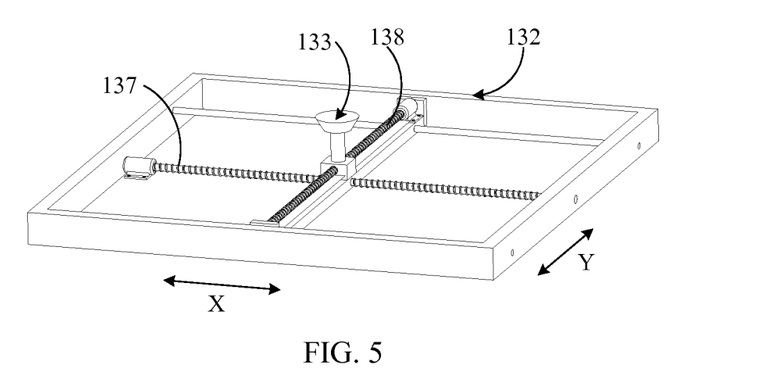
FIG. 5 is a schematic view showing the structure of the driving assembly of the cartridge of FIG. 4.

FIG. 4 is a perspective view of the cartridge of the warehouse system of FIG. 1. FIG. 5 is a schematic view showing the structure of the driving assembly of the cartridge of FIG. 4. As shown in FIGS. 4 and 5, the cartridge 13 includes a detecting module 131 having a driving assembly 132, a detecting probe 133, a particle detector 134, a communication module 135, and an elastic tube 136.

In the embodiment, the normal storage locations 112 and the abnormal storage locations 113 are determined by detecting the air particles of the storage locations 111 in accordance with the above-mentioned process. The transmitting assembly 14 transports the cartridge 13 to the abnormal storage locations 113 so that the detecting module 131 of the cartridge 13 may detect the air particles on the surface of the air filter 12 of the corresponding abnormal storage locations 113.

In the embodiment, the driving assembly 132 drives the detecting probe 133 to move. The driving assembly 132 includes a first driving component 137 and a second driving component 138. The first driving component 137 drives the detecting probe 133 along a first direction X, and the second driving component 138 drives the detecting probe 133 along a second direction Y. Specifically, the second driving component 138 is installed on the first driving component 137, and the detecting probe 133 is installed on the second driving component 138. The first driving component 137 drives the detecting probe 133 and the second driving component 118 move along the X direction together, and the second driving component 138 drives the detecting probe 133 to move along the Y direction. In the embodiment, the first direction X is orthogonal to the second direction Y.

It is to be noted that the location of the driving assembly 132 may be adjusted in accordance with the location of the air filter 12. As shown in FIG. 4, the driving assembly 132 is installed on an internal surface of the cartridge 13 when the air filter 12 is arranged on the ceiling of the warehouse 11. In other embodiments, the driving assembly 132 may be installed on a side portion of the cartridge 13 when the air filter 12 is arranged on the internal surface of the storage locations 111. It is understood that the cartridge 13 may include two driving assemblies 132 so as to facilitate the operation of the driving assembly 132. And the two driving assembles 132 may be arranged on the top or side portion of the cartridge 13.

Figure 6:
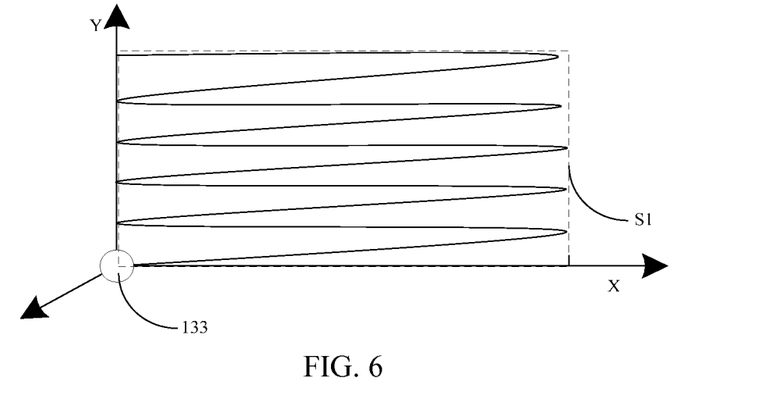
FIG. 6 is a schematic view showing the moving path of the driving assembly of FIG. 5.

The detecting probe 133 absorbs the air particles on the surface of the corresponding air filter 12 of the abnormal storage locations 113. Preferably, the detecting probe 133 moves along a sinusoidal path (as shown in FIG. 6) when driven by the first driving component 137 and the second driving component 138. In order to precisely detect the air particles, the distance between a top of the detecting probe 133 and the top portion of the air filter 12 is of a range between 50 mm to 100 mm. In addition, the dimension of the moving area of the detecting probe 133 equals to that of the an filter 12.

It is to be noted that the detecting probe 133 is arranged on the top portion or the cartridge 13 before the detecting process begins. When the detecting process begins, the top 1331 of the detecting probe 133 rotates through 90 degrees and then rises up above the surface of the cartridge 13.

In the embodiment the particle detector 134 connects with the detecting probe 133 by the elastic tube 136 so as to receive the air particles absorbed by the detecting probe 133. In addition, the particle detector 134 calculates the radius of the air particles and transmits the radius to the communication modulo 135.

The communication module 135 may be a wireless access point for transmitting the radius of the air particles to the control base 15. Referring to FIG. 1, the wireless base station 16 is installed within the warehouse 11, and the forwarder 17 is installed between two adjacent warehouses 11. The control base 15 may be a computer arranged in an outside of the warehouse 11. One or a plurality of wireless base stations 16 are arranged according to the distance between the warehouses 11. After obtaining the radius of the air particles transmitted by the particle detector 134, the communication module 135 of the detecting module 131 transmits the radius to the control base 15 via the wireless network established by the wireless base station 16 and the forwarder 17. As such, the control base 15 determines if the corresponding air titter 12 of the abnormal storage locations 113 has leaked.

In the embodiment, the control base 15 saves the radius of the air particles detected by the detecting module 131, and calculates the accumulative air particles within the predetermined particle radius so as to determine ii the amount of the accumulative air particles is larger than the threshold. If yes, the control base 15 determines that the corresponding air filter 12 of the abnormal storage locations 113 has leaked and has to be maintained. If no, the control base 15 determines that the corresponding air filter 12 of the abnormal storage locations 113 has not leaked.

For example, the amount of the accumulative air particles within the radius ranging from 0 to $0.3\mu$, ranging from $0.3\mu$ to $0.5\mu$, and ranging from 0.5 to $10\mu$ are respectively 25, 11, and 0. It can be seen from Table 1 that the corresponding threshold of the above radius range are 30, 10, and 0. When the amount of the accumulative air particles within the radius ranging from 0 to $0.3\mu$ and from 0.5 to $10\mu$ is less than or equal to the corresponding threshold, and the amount of the accumulative air particles within the radius ranging from 0.3 to $0.5\mu$ is larger than the corresponding threshold, the control base 15 determines that the corresponding air filter 12 of the abnormal storage locations 113 has leaked.

It is to be noted that the control base 15 determines that the corresponding air filter 12 of the abnormal storage locations 113 has leaked when the amount of the accumulative air particles within the ranges in Table 1 are less than or equal to the corresponding threshold, but the total amount of the accumulative air particles is larger than the sum in Table 1. For example, when the amount of the accumulative air particles within the radius ranging from 0 to $0.3\mu$, ranging from $0.3\mu$ to $0.5\mu$, and ranging from 0.5 to $10\mu$ are respectively 25, 10, and 0, it can be seen that the amount of the accumulative air particles within the ranges in Table 1 are less than or equal to the corresponding threshold. However, the total amount of the accumulative air particles is 35, which is larger than the sum for the "10-class," which is listed in the rightmost column in Table 1. Under the circumstance, the control base 15 determines that the corresponding air filter 12 of the abnormal storage locations 113 has leaked. It is to be understood that the same rules may be applied to "100-class" or "1000-class."

It is to be noted that when the detecting process for one air filter 12 of the abnormal storage locations 113 within the warehouse 1 is completed, the transmitting assembly 14 transmits the cartridge 13 to another warehouse 11.

The operations of the system for detecting air particles will be described hereinafter.

Figure 7:
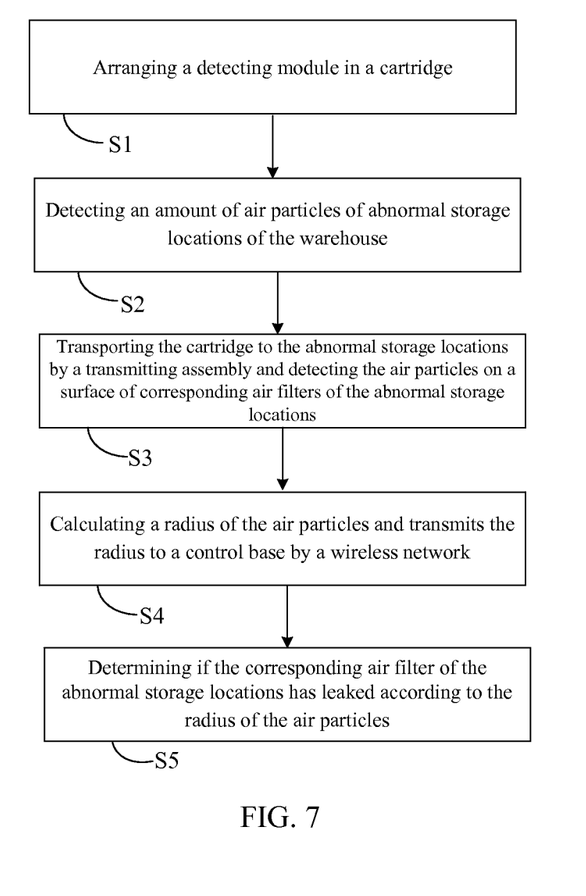
FIG. 7 is a flowchart illustrating the method for detecting the air particles in accordance with a second embodiment.

FIG. 7 is a flowchart illustrating the method for detecting the air particles in accordance with a second embodiment. The method includes the following steps. In step S1, the detecting module is arranged in the cartridge. In step S2, the detecting module determines the storage locations with the excessive amount of air particles. Each warehouse includes a plurality of storage locations. As warehouse systems require a dust free environment, it is needed to detect the air particles in each storage locations of the warehouse periodically. In real scenario, the particle detector of the PMS system extracts gas equaling to one cubit foot so as to calculate the accumulative air particles within the predetermined particle radius. One storage location is determined as abnormal when the amount of the accumulative air particles is larger than a threshold. The values of the thresholds are listed in Table 1.

In step S3, the cartridge is transported to the abnormal storage locations by the transmitting assembly such that the air particles of the corresponding air filter of the abnormal storage locations are detected. After the detection for one abnormal storage locations is completed, the cartridge is then transported to next abnormal storage location until the detection has been conducted for all of the abnormal storage locations.

In step S4, the detecting module calculates the radius of the air particles and transmits the radius to the communication module. It is to be noted that the detecting module calculates the radius upon completing the detecting process for one abnormal storage locations.

In step S5, the control base determines if the corresponding air filter of the abnormal storage locations has leaked according to the radius of the air particles. The control base saves the radius of the air particles detected by the detecting module, and calculates the accumulative air particles within the predetermined particle radius to determine if the amount of the accumulative air particles is larger than the threshold. If yes, the control base determines that the corresponding air filter of the abnormal storage locations has leaked. If no, the control base determines that the corresponding air filter of the abnormal storage locations has not leaked.

Figure 8:
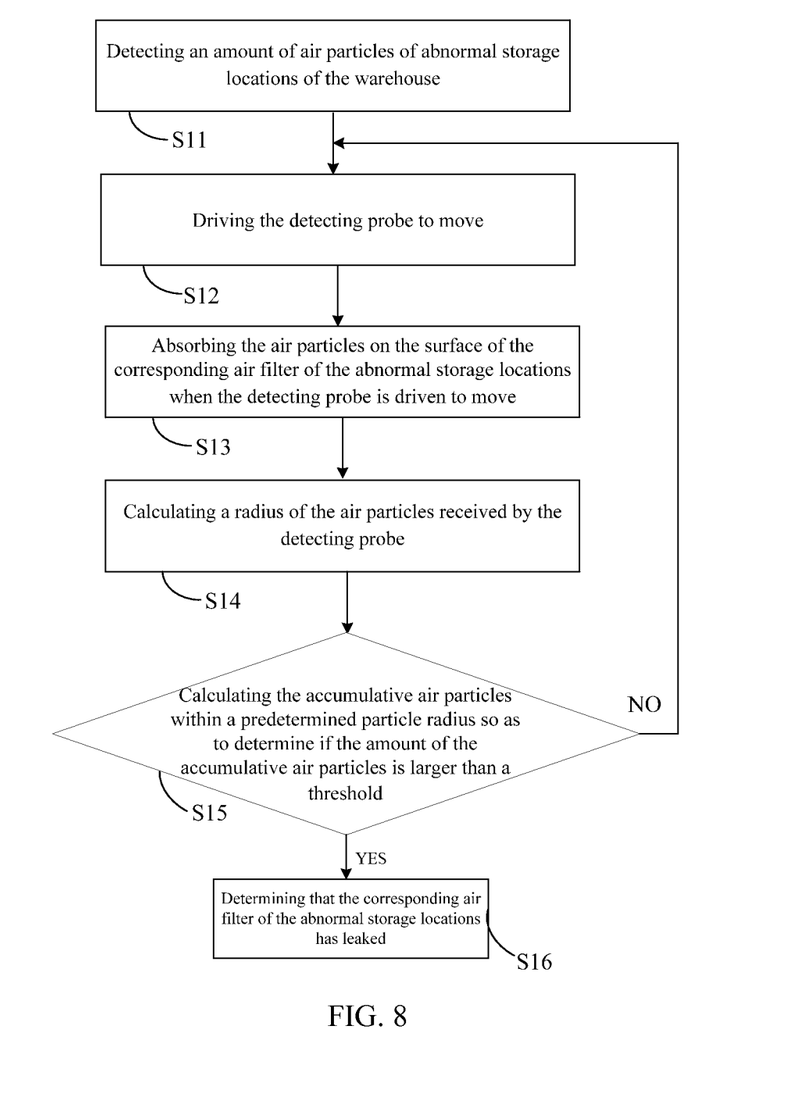
FIG. 8 is a flowchart illustrating the method for detecting the air particles in accordance with another embodiment.

FIG. 8 is a flowchart illustrating the method for detecting the air particles in accordance with another embodiment. The method includes the following steps. In step S11, the detecting module determines the storage locations with excessive amount of air particles. In step S12, the detecting probe is driven to move. The detecting module includes a driving assembly, a detecting probe, a particle detector, a communication module, and an elastic tube. First, the cartridge is transported to the abnormal storage locations by the transmitting assembly. Second, the driving assembly drives the detecting probe to move. The operations of the driving assembly and the detecting probe are substantially similar to those disclosed in the first embodiment.

In step S13, the detecting probe absorbs the air particles on the surface of the corresponding air filter of the abnormal storage locations.

In step S14, the particle detector calculates the radius of the air particle absorbed by the detecting probe. In this step, the particle detector first receives the air particles absorbed by the detecting probe, and then calculates the radius of the air particle.

In step S15, the control base calculates the accumulative air particles within the predetermined particle radius so as to determine if the amount of the accumulative air particles is larger than the threshold. It yes, the process goes to step S16. If no, the process returns to step S12, and the detection process is conducted for the next abnormal storage locations 113.

In step S16, the control base determines that the corresponding air filter of the abnormal storage locations has leaked. Upon determining that the air filter has leaked, the air filter has to be maintained.

In view of the above, the system for detecting air particles may detect the air particles on the surface of the air filter of the corresponding abnormal storage locations by the cartridge with the detecting module. The control base determines if the air filter has leaked according to the received detecting results. Comparing to the typical detecting process conducted by human labors, the detecting process of the present embodiments is safer, more precise and convenient.

It is believed that the present embodiments and their advantages will be understood from the foregoing description, and it will be apparent that various changes may be made thereto without departing from the spirit and scope of the invention or sacrificing all of its material advantages, the examples hereinbefore described merely being preferred or exemplary embodiments of the invention.

What is claimed is:

1. A method for detecting air particles in a warehouse having a plurality of storage locations, comprising:
   arranging a detecting module in a cartridge having a shape substantially the same with the storage location;
   a first detecting step detecting an amount of air particles of abnormal storage locations of the warehouse;
   transporting the cartridge to the abnormal storage locations by a transmitting assembly;
   a second detecting step detecting the air particles on a surface of corresponding air filters of the abnormal storage locations;
   calculating a radius of the air particles and transmitting the radius to a control base by a communication module;
   determining if the corresponding air filter of the abnormal storage locations has leaked according to the radius of the air particles;
   wherein the detecting module comprises a detecting probe being arranged on a top portion of the cartridge and a particle detector, and the second detecting step further comprises:
   a top of the detecting probe rising up for 90 degrees so as to be above the top portion of the cartridge;
   driving the detecting probe to move;
   absorbing the air particles on the surface of the corresponding air filter of the abnormal storage locations when the detecting probe is driven to move, the particle detector being connected with the detecting probe by an elastic tube to receive the air particles absorbed by the detecting probe;
   the determining step further comprises:
   saving the radius of the air particles detected by the detecting module, and calculating the accumulative air particles within a predetermined particle radius so as to determine if the amount of the accumulative air particles is larger than a threshold larger than zero; and
   determining that the corresponding air filter of the abnormal storage locations has leaked if the amount of the accumulative air particles is larger than the threshold.

2. The method as claimed in claim 1, wherein a dimension of the moving area of the detecting probe equals to the dimension of the air filter.

3. A method for detecting air particles in a warehouse having a plurality of storage comprising:
   arranging a detecting module in a cartridge having a shape substantially the same with the storage location;
   a first detecting step detecting an amount of air particles of abnormal storage locations of the warehouse;
   transporting the cartridge to the abnormal storage locations by a transmitting assembly;
   a second detecting step detecting the air particles on a surface of corresponding air filters of the abnormal storage locations, wherein the detecting module comprising a detecting probe being arranged on a top portion of the cartridge and a particle detector, the particle detector being connected with the detecting probe by an elastic tube to receive the air particles absorbed by the detecting probe, and the second detecting step further comprises:
   a top of the detecting probe rising up for 90 degrees so as to be above the top portion of the cartridge;
   driving the detecting probe to move; and
   absorbing the air particles on the surface of the corresponding air filter of the abnormal storage locations when the detecting probe is driven to move;
   calculating a radius of the air particles and transmitting the radius to a control base by a communication module; and
   determining if the corresponding air filter of the abnormal storage locations has leaked according to the radius of the air particles.

4. The method as claimed in claim 3, wherein the determining step further comprises:
   saving the radius of the air particles detected by the detecting module, and calculating the accumulative air particles within a predetermined particle radius so as to determine if the amount of the accumulative air particles is larger than a threshold larger than zero; and
   determining that the corresponding air filter of the abnormal storage locations has leaked if the amount of the accumulative air particles is larger than the threshold.

5. The method as claimed in claim 3, wherein a dimension of the moving area of the detecting probe equals to the dimension of the air filter.

6. A warehouse system for detecting air particles, comprising:
   a warehouse comprising a plurality of storage locations, wherein the storage locations comprises abnormal storage locations with an excessive amount of air particles;
   air filters correspondingly arranged on outer sides of each storage location for filtering the air particles in the storage locations;
   a cartridge having a shape substantially the same with the storage location, the cartridge comprising a detecting module, and the detecting module further comprising a driving assembly, a detecting probe being arranged on a top portion of the cartridge, a particle detector, and a communication module, wherein:
   a top of the detecting probe rising up for 90 degrees so as to be above the top portion of the cartridge;
   the driving assembly drives the detecting probe to move;
   the detecting probe is for absorbing the air particles on the surface of the corresponding air filter of the abnormal storage locations when the detecting probe is driven to move;
   the particle detector being connected with the detecting probe by an elastic tube to receive the air particles absorbed by the detecting probe, to calculate the radius of the air particles detected by the detecting probe, and to transmit the radius to the communication module;

the communication module transmits the radius to the control base via wireless communications;

a transmitting assembly for transporting the cartridge to the abnormal storage locations such that the detecting module detects the air particles on a surface of the air filters of the corresponding abnormal storage locations;

wherein the detecting module further calculates a radius of the air particles and transmits the radius of the air particles to a control base; and the control base determines if the corresponding air filter of the abnormal storage locations has leaked.

7. The system as claimed in claim 6, wherein the control base saves the radius of the air particles detected by the detecting module, and calculates the accumulative air particles within the predetermined particle radius to determine if the amount of the accumulative air particles is larger than a threshold larger than zero; and the control base determines that the corresponding air filter of the abnormal storage locations has leaked if the amount of the accumulative air particles is larger than the threshold.

8. The system as claimed in claim 6, wherein a distance between the top of the detecting probe and a top portion of the air filter is of a range between 50 mm to 100 mm.

9. The system as claimed in claim 6, wherein the driving assembly comprises a first driving component and a second driving component, the first driving component drives the detecting probe along a first direction, the second driving component drives the detecting probe along a second direction, and the first direction is orthogonal to the second direction.

10. The system as claimed in claim 6, wherein a dimension of the moving area of the detecting probe equals to the dimension of the air filter.

11. The system as claimed in claim 6, wherein the driving assembly is installed on a top portion of the cartridge.

12. The system as claimed in claim 6, wherein the driving assembly is installed on a side portion of the cartridge.

* * * * *